US010625233B2

(12) United States Patent
Evans et al.

(10) Patent No.: US 10,625,233 B2
(45) Date of Patent: Apr. 21, 2020

(54) TESTING PHARMACEUTICALS AND RELATED SUBSTANCES

(71) Applicants: Jonathan C. Evans, Midland, MI (US); Derrick D. Hilliker, Midland, MI (US); Theodore W. Selby, Midland, MI (US)

(72) Inventors: Jonathan C. Evans, Midland, MI (US); Derrick D. Hilliker, Midland, MI (US); Theodore W. Selby, Midland, MI (US)

(73) Assignee: Tannas Company, Midland, MI (US)

( * ) Notice: Subject to any disclaimer, the term of this patent is extended or adjusted under 35 U.S.C. 154(b) by 24 days.

(21) Appl. No.: 15/932,658

(22) Filed: Apr. 3, 2018

(65) Prior Publication Data

US 2018/0326385 A1 Nov. 15, 2018

Related U.S. Application Data

(60) Provisional application No. 62/601,955, filed on Apr. 4, 2017.

(51) Int. Cl.
*G01N 25/20* (2006.01)
*G01N 25/22* (2006.01)
(Continued)

(52) U.S. Cl.
CPC ........... *B01J 19/0013* (2013.01); *B01J 19/02* (2013.01); *B01L 9/06* (2013.01); *G01N 25/20* (2013.01);
(Continued)

(58) Field of Classification Search
CPC ........ G01N 33/15; G01N 25/20; G01N 25/22; G01N 25/26
See application file for complete search history.

(56) References Cited

U.S. PATENT DOCUMENTS 6,015,532 A * 1/2000 Clements ............... G01N 35/02
422/510
7,678,328 B1 3/2010 Secrist et al.
(Continued)

OTHER PUBLICATIONS

Xu, F., et al. "Low-temperature heat capacities and standard molar enthalpy of formation of aspirin." Journal of thermal analysis and calorimetry 76.2 (2004): 481-489.*
(Continued)

*Primary Examiner* — Herbert K Roberts
(74) *Attorney, Agent, or Firm* — Christopher John Rudy

(57) ABSTRACT

An active pharmaceutical ingredients (API) or related substance (RS) can be tested for stability by placing the API or RS in an instrument containing a pressure-controllable atmosphere, controlling the pressure of the atmosphere in the instrument for a predetermined time, and evaluating the API or RS for stability. Testing can be carried out also at predetermined temperature(s) and/or under the influence of gaseous trigger(s) and so forth. For instance, an API sample can be placed in a bomb test instrument/reactor, oxygen as a gaseous trigger can be introduced to contact the API sample under constant and/or ramped temperature(s) and elevated pressure(s) for predetermined time(s), and the API sample can be evaluated for stability. An insert carousel may hold a sample of API(s) and/or RS(s) and/or aliquot(s) of sample(s) of API(s) and/or RS(s) for insertion into the bomb test instrument/reactor.

12 Claims, 3 Drawing Sheets

(51) Int. Cl.
*G01N 25/26* (2006.01)
*G01N 33/15* (2006.01)
*B01J 19/00* (2006.01)
*B01J 19/02* (2006.01)
*G01N 31/00* (2006.01)
*B01L 9/06* (2006.01)
*G01N 35/00* (2006.01)
*B01L 7/00* (2006.01)
*B01L 1/02* (2006.01)

(52) U.S. Cl.
CPC ............ *G01N 25/22* (2013.01); *G01N 25/26* (2013.01); *G01N 31/00* (2013.01); *G01N 33/15* (2013.01); B01J 2219/00011 (2013.01); B01J 2219/00132 (2013.01); B01L 1/025 (2013.01); *B01L 7/52* (2013.01); B01L 2200/147 (2013.01); B01L 2400/0409 (2013.01); G01N 2035/00099 (2013.01)

(56) References Cited

U.S. PATENT DOCUMENTS

| | | |
|---|---|---|
| 8,679,405 B1 | 3/2014 | Secrist et al. |
| 8,975,083 B2 | 3/2015 | Selby et al. |
| 2003/0162226 A1* | 8/2003 | Cima .................. B01J 19/0046 435/7.1 |
| 2017/0205355 A1 | 7/2017 | Selby et al. |
| 2017/0284994 A1 | 10/2017 | Evans et al. |

OTHER PUBLICATIONS

Evans et al., U.S. Appl. No. 62/601,955 entitled, "Testing Pharmaceuticals and Related Substances," filed Apr. 4, 2017 A.D.
Evans et al., U.S. Appl. No. 62/390,774 entitled "Oxidation of Grease," filed Apr. 8, 2016 A.D.
Selby et al., U.S. Appl. No. 14/121,952 entitled "Grease Oxidation," filed Nov. 6, 2014 A.D.
ICH Harmonised Tripartite Guideline, "Stability Testing of New Drug 7 Substances and Products, Q1A(R2)," Step 4 version, Feb. 6, 2003.
ICH Harmonised Tripartite Guideline, "Validation of Analytical Procedures: Text and Methodology Q2(R1)," Step 4 version, Oct. 27, 1994.
United States Pharmacopeial Convention, USP 39, Aug. 1, 2016, General Chapters 1225 and 1226, "Validation of Compendial Procedures," pp. 1640-1645, and "Verification of Compendial Procedures," p. 1646.
Blessy et al., *J. Pharm. Anal.*, 2014;4(3): 159-165, "Development of forced degradation and stability indicating studies of drugs—a review."

* cited by examiner

TESTING PHARMACEUTICALS AND RELATED SUBSTANCES

This claims domestic priority benefits under 35 USC 119(e) of provisional patent application No. 62/601,955 filed on Apr. 4, 2018 A.D.

FIELD AND PURVIEW OF THE INVENTION

This concerns a method and apparatus for testing pharmaceutical and related substances. Temperature, pressure, gaseous trigger(s), and so forth can be controlled for testing. For example, gaseous Oxygen under isothermal pressure in a bomb test instrument/reactor—such as found in U.S. Pat. No. 7,678,328 B1, U.S. Pat. No. 8,679,405 B1 and U.S. Pat. No. 8,975,083 B2, and U.S. patent application Ser. No. 14/121,952 and U.S. 62/390,774, which further thereto may include a special insert carousel for holding sample aliquot vials—can be applied to a sample for a predetermined time and evaluated.

BACKGROUND TO THE INVENTION

Stability of pharmaceuticals is an ongoing concern. Of great concern to the Food and Drug Administration (FDA), moreover, is oxidative stability of active pharmaceutical ingredients (APIs). The reason that the FDA is so concerned is because oxidative stability can adversely affect the bioavailability of an API, for example, by decreasing or increasing bioavailability of the API from bodily absorption, and may potentially produce new material(s) that could be toxic.

In the last twenty years, there has been a shift in mindset in the pharmaceutical industry. Thus, for example, for many years, the industry shied away from semi-crystalline APIs owing to concerns about the stability of their amorphous content since, in some cases, an API compound may form different polymorphs, each of which has a different level of stability generally related to its energy state, and, with temperature and time, the API may convert between polymorphs, which can affect bioavailability. Generally, if given enough time, such polymorphic substances settle at the lowest ground state polymorph form. Be that as it may, owing to the number of new experimental drug candidates having poor water solubility and thus, in general, low bioavailability, the industry has developed technology intended to help stabilize these types of materials. Typically this is done by blending the API with an excipient such as a polymer generally recognized as safe, i.e., a GRAS approved polymer, which stabilizes the polymorph; or by producing the polymorph in the presence of a stabilizing polymer. These substances need testing to help verify that they are safe and effective.

Accordingly, the testing of pharmaceuticals and pharmaceutical candidates is critical. The most common way for evaluation oxidative stability of an API is to place it in an open vial in an oven, heat it at a set temperature, for example, about 40° C., 50° C., 60° C. or 80° C., and periodically remove samples from the vial for high pressure liquid chromatography (HPLC) analysis. Another common way for evaluation API oxidative stability is to add a small amount 35% hydrogen peroxide directly to the sample with API in an open vial, and, as above, place it in an oven, apply heat, and periodically remove samples for HPLC analysis. Both of these procedures are time consuming. For an oxidatively stable API, it can take months to show an appreciable amount of oxidation.

As necessary as oxidative stability testing of new APIs is to the pharmaceutical industry, however, specific, reliable protocols for the same appear to be lacking, yet still needed. Note, ICH Harmonised Tripartite Guidelines, "Stability Testing of New Drug Substances and Products, Q1A(R2)," Step 4 version dated 6 Feb. 2003; "Validation of Analytical Procedures: Text and Methodology Q2(R1)," Step 4 version parent guideline dated 27 Oct. 1994 (complementary guideline on methodology dated 6 Nov. 1996 incorporated in November 2005); United States Pharmacopeial Convention, USP 39, Aug. 1, 2016, General Chapters 1225 and 1226, "Validation of Compendial Procedures," pages 1640-1645, and "Verification of Compendial Procedures," page 1646; and Blessy et al., *J. Pharm. Anal.*, 2014; 4(3): 159-165, "Development of forced degradation and stability indicating studies of drugs—a review."

It would be desirable to improve upon the art; to ameliorate if not solve problem(s) in it, to include as aforesaid; and particularly to enhance oxidation testing of APIs and reduce the time and increase the reliability of such testing. It would be desirable to provide the art an alternative.

A FULL DISCLOSURE OF THE INVENTION

Provided in one aspect is a method of testing an API or related substance (RS) for stability comprising placing the API or RS in an instrument containing a pressure-controllable atmosphere, controlling the pressure of the atmosphere in the instrument for a predetermined time, and evaluating the API or RS for stability. Testing can be carried out also at predetermined temperature(s) and/or under the influence of gaseous trigger(s) and so forth. For instance, an API sample can be placed in a bomb test instrument/reactor, oxygen as a gaseous trigger can be introduced to contact the API sample under constant and/or ramped temperature(s) and elevated pressure(s) for predetermined time(s), and the API sample can be evaluated for stability. The bomb test instrument/reactor can be such as disclosed or employed in U.S. Pat. No. 7,678,328 B1, U.S. Pat. No. 8,679,405 B1 and U.S. Pat. No. 8,975,083 B2, and U.S. patent application Ser. No. 14/121,952 and U.S. 62/390,774. Provided in further aspects are an insert carousel for holding a sample of API(s) and/or RS(s) and/or aliquot(s) of sample(s) of API(s) and/or RS(s) for insertion into the bomb test instrument/reactor; and, in combination, the insert carousel and bomb test instrument/reactor.

The invention is useful in testing pharmaceuticals and related compounds.

Significantly, by the invention, the art is advanced in kind, and problem(s) in the art, to include as noted above, is(are) ameliorated if not solved. The art is provided alternative(s). More particularly, oxidation testing of APIs is enhanced, and the time required for the testing can be reduced, which can not only save time but also money. A new use and auxiliary equipment for bomb test instrument/reactor devices—such as the rotatable bomb devices disclosed or employed in U.S. Pat. No. 7,678,328 B1, U.S. Pat. No. 8,679,405 B1 and U.S. Pat. No. 8,975,083 B2, and U.S. patent application Ser. No. 14/121,952 and U.S. 62/390,774—are provided, which increases the versatility of such devices. As well, the reliability of such testing can be greatly increased, noting, among other things, the precise temperature control available from these rotatable bombs. Several advantages over the commonly employed techniques, which employ air at ambient pressure and a temperature that may not be strictly controlled, include the following:

As a gaseous trigger, pure oxygen, a chalcogen, can be employed to help accelerate oxidation; or another atmosphere can be employed as a gaseous trigger to test for special interactions such as use of carbon dioxide gas; another chalcogen such as gaseous sulfur; halide(s) in gaseous form such as gaseous fluorine, chlorine, bromine and/or iodine; a potentially inert gas such as pure nitrogen, helium or argon; a reducing gas; an acidic gas; a basic gas; an organic compound in a gaseous state; a mixture of gasses such as air, or a mixture of any of the foregoing, for example, air with gasoline vapor, and so forth and the like.

Increased pressure can be employed to accelerate the rate of reaction; decreased pressure may be employed; the pressure may be constant and/or ramped.

Heating can be provided at precise temperatures, at constant and/or ramped value(s).

Thus, in addition to saving time and money, the present method and apparatus can potentially allow the pharmaceutical scientist to discover oxidative metabolite(s) that could be detrimental or perhaps even beneficial, which would not be easily discovered by the aforementioned conventional oxidative stability testing techniques. The invention is simple, but highly effective.

Numerous further advantages attend the invention.

The drawings form part of the specification hereof. With reference to the drawings, which are not necessarily drawn to scale, the following is briefly noted:

Figure 1:
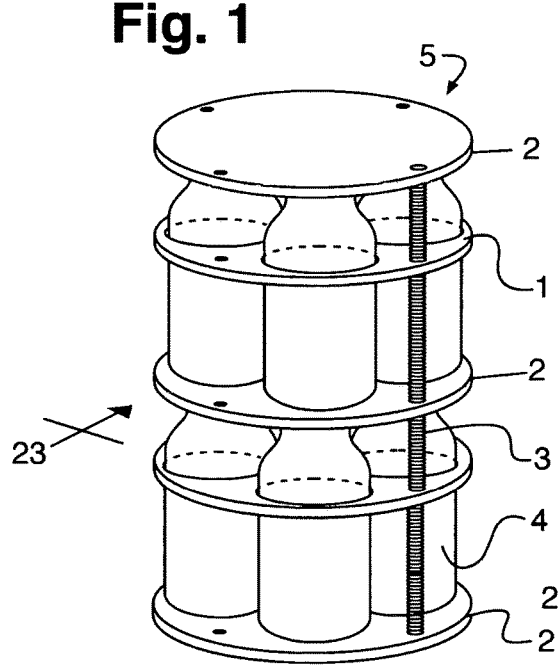
FIG. 1 is a top perspective view of an insert carousel with illustrative sample aliquot vials.
Figure 3:
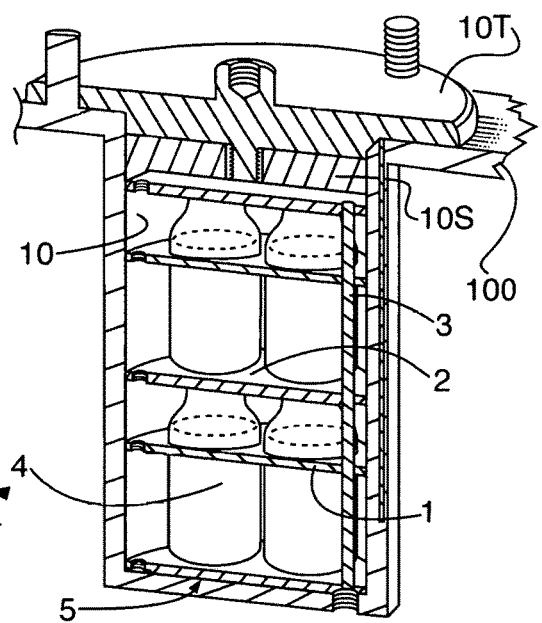
Figure 2:
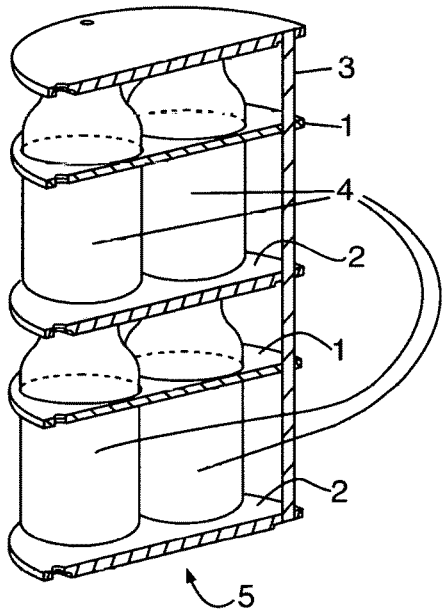
FIG. 2 is a top perspective sectional view of the insert carousel with sample aliquot vials as depicted in FIG. 1, taken along 23-23 in FIG. 1.

FIG. 3 is a top perspective sectional view of the insert carousel with sample aliquot vials as depicted in FIG. 2, also taken along 23-23 in FIG. 1, inserted into the hollow interior bomb of a bomb test instrument/reactor device—such as the rotatable bomb devices disclosed or employed in U.S. Pat. Nos. 7,678,328 B1, 8,679,405 B1 and 8,975,083 B2, and U.S. patent application Ser. No. 14/121,952 and U.S. 62/390,774—and having its upper cap and a spacer in place, ready for testing.

Figure 4:
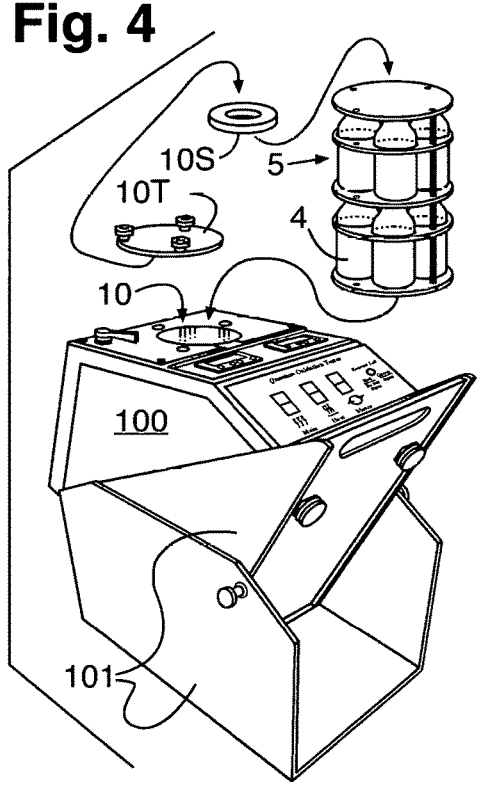

FIG. 4 is a top perspective exploded plan view of the insert carousel with aliquot vials as shown in FIG. 1, for inserting into the hollow interior bomb of a bomb test instrument/reactor device with stand, i.e., pivotable, cradling framework, as disclosed in U.S. patent application Ser. No. 14/121,952 and also employed in patent application No. U.S. 62/390,774 with the pivotable, cradling framework pivoted so that the cylindrical hollow interior bomb is oriented vertically along an imaginary central axis whereof such that the insert carousel with sample aliquot vials is oriented vertically for testing.

Figure 5:
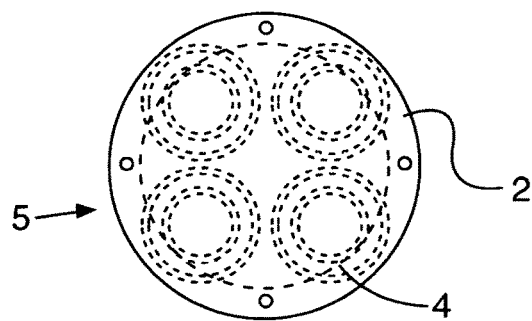
Figure 6:
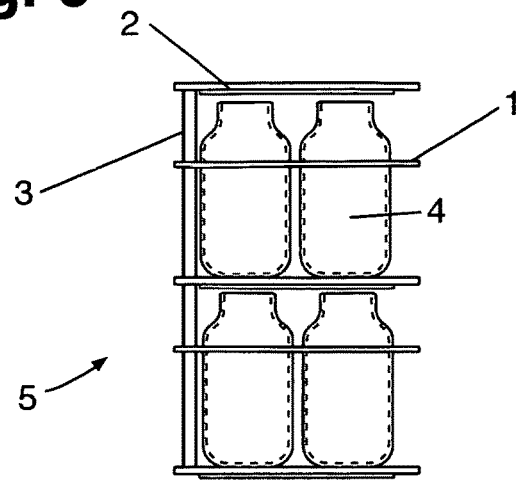
Figure 7:
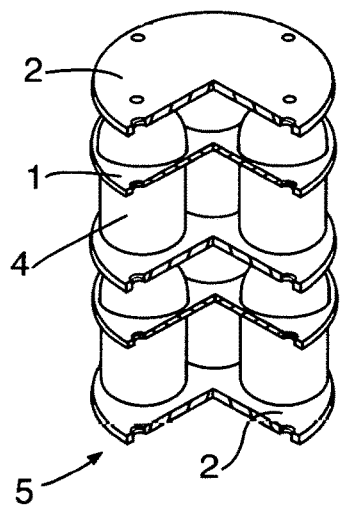

FIGS. 5-7 are top plan, elevational, and top perspective sectional views, respectively, of an insert carousel of the invention with sample aliquot vials. Compare with FIG. 1.

Figure 8:
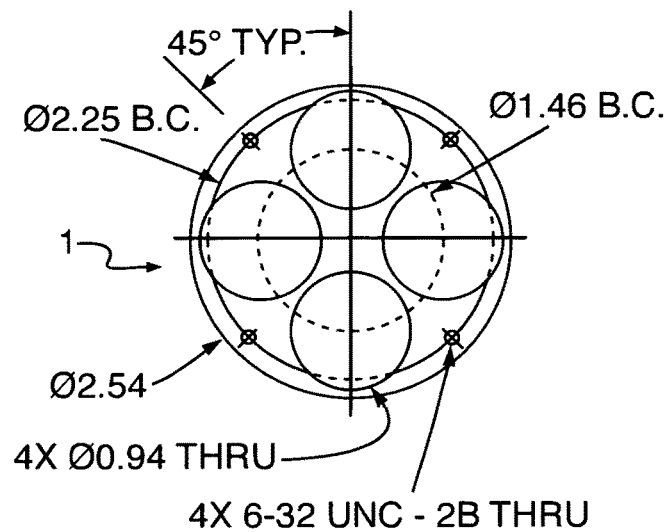
Figure 9:
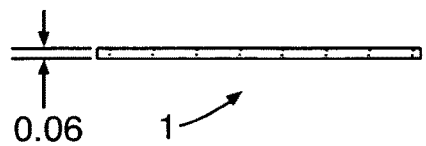
Figure 10:
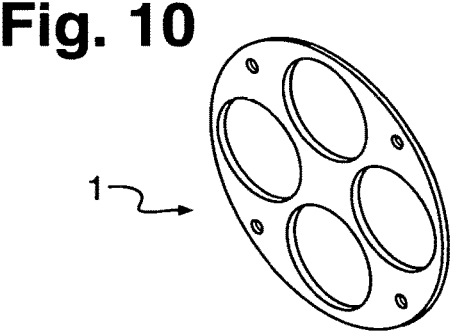

FIGS. 8-10 are top plan, elevational, and perspective sectional views, respectively, of one of the two the sample aliquot vial retainer plates of the insert carousel in FIGS. 5-7.

Figure 11:
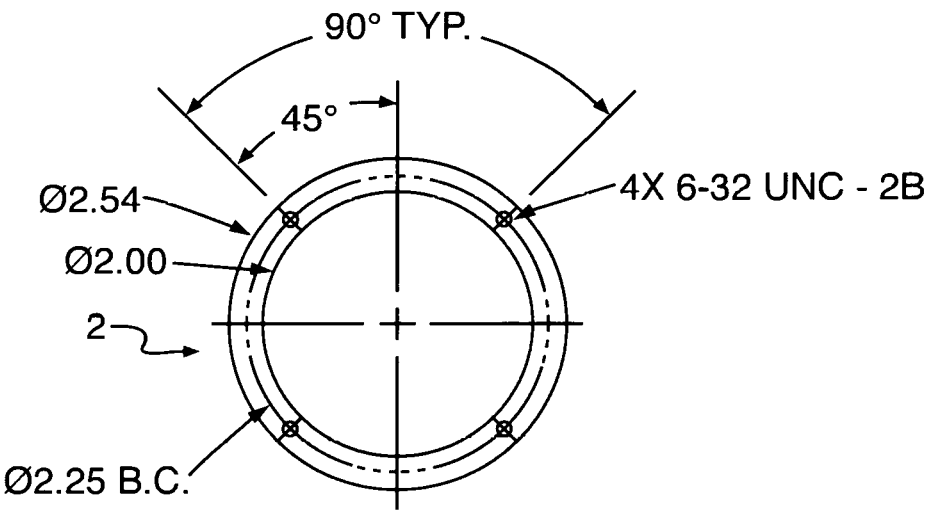
Figure 12:
Figure 13:
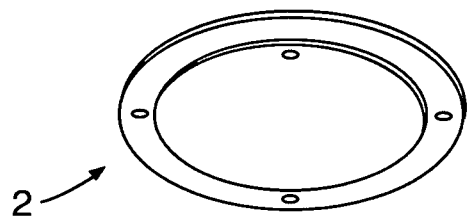

FIGS. 11-13 are top plan, elevational, and perspective sectional views, respectively, of one of the three the sample aliquot vial top/bottom plates of the insert carousel in FIGS. 5-7.

Figure 14:
Figure 15:
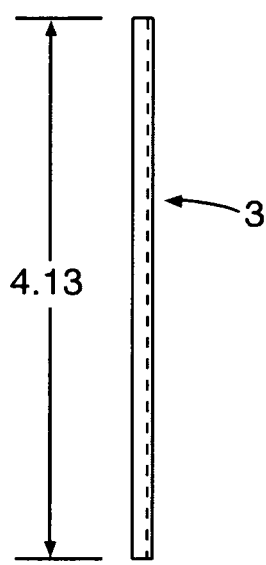
Figure 16:
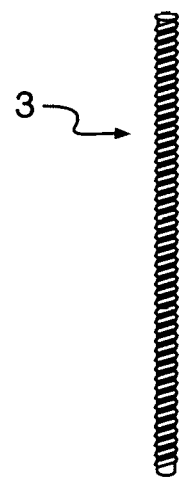

FIGS. 14-16 are top plan, elevational, and perspective sectional views, respectively, of the threaded connecting shaft of the insert carousel in FIGS. 5-7.

The following list is a key to reference numerals found in the drawing figures:

Number Remarks
 1 Sample aliquot vial retainer
 2 Sample aliquot vial top or bottom plate
 3 Threaded connecting shaft
 4 Sample aliquot vial
 5 Insert carousel
 10 Hollow bomb housing
 10S Hollow bomb spacer for insert carousel
 10T Hollow bomb housing lid
 100 Rotating bomb device disclosed or employed in U.S. Pat. Nos. 7,678,328 B1, 8,679,405 B1 and 8,975,083 B2, and U.S. patent application Ser. No. 14/121,952 and U.S. 62/390,774
 101 Pivotable, cradling framework, as disclosed in U.S. patent application Ser. No. 14/121,952 and also employed in patent application No. U.S. 62/390,774.

The invention can be further understood by the following additional detail set forth below, which may be read in view of the drawings. As with the foregoing, the following is to be understood in an illustrative and not necessarily limiting sense.

For use in evaluating the oxidative stability of an API or RS the bomb test instrument/reactor device 100 with pivotable, cradling framework 101, which is commercially available from Tannas Company, Midland, Mich. as the Quantum® rotatable bomb test instrument, beneficially is placed in the vertical position as in the manner it is employed for grease oxidation testing (ASTM D942) as found in U.S. patent application Ser. No. 14/121,952 and U.S. 62/390,774. Insert carousel 5—which can be assembled conveniently from parts: two sample aliquot vial retainers 1, for example, made of #316 stainless steel; three sample aliquot vial top or bottom plates 2, for example, made of #316 stainless steel; and one or more threaded connecting shaft(s) 3, for example, made of #316 stainless steel, each threaded through correspondingly threaded holes in the retainers 1 and plates 2—can hold one or more sample aliquot vial(s) 4 typically employed otherwise in the art to evaluate oxidative stability, say, eight in total with four in a lower level and four in an upper level of the insert carousel 5, each sample aliquot vial 4 able to contain an API and/or RS for evaluation of its oxidative stability and/or other property(ies). The carousel 5 may be configured to accommodate more or less sample aliquot vials 4, say, six sample aliquot vials 4 larger than those depicted in two levels; ten, twelve or fourteen sample aliquot vials 4 smaller than those depicted in two levels; or fifteen, eighteen or twenty-one sample aliquot vials 4 smaller than those depicted in three levels; and so forth. The insert carousel 5 is configured with appropriate head space at each level so as to ensure good exposure to the gaseous trigger, for example, elemental oxygen. Removal of an upper level of or provision of greater head space above a set of sample aliquot vials 4 may provide for emplacement of stirring apparatus, particularly when the sample to be tested is a liquid rather than a powder or other solid. When loaded with sample aliquot vial(s) 4, the insert carousel 5 is inserted into the hollow bomb housing 10 of the bomb test instrument/reactor device 100 with pivotable, cradling framework 101 orienting the hollow bomb housing 10 vertically. Hollow bomb spacer 10S, made of any suitable material, for example, Teflon® polytetrafluoroethylene, may be placed on top of the insert carousel 5 loaded with properly filled sample aliquot vials 4 to keep the carousel with its sample(s) from moving up and down undesirably, and bomb conditions can be established after sealing with hollow bomb housing lid 10T.

Dimensions or angles set forth in the figures are exemplary, with dimensions in inches and angles in degrees. They may be considered to be approximate, to have typical engineering deviations, or even to be exact. All edges of parts 1, 2, 3 of the insert carousel 5 may be broken and deburred.

In an exemplary employment, rates of oxidation of an API are determined readily with the aforementioned devices 100, 101 and carousel 5. Once a rate of oxidation for the API is known, then it may be determined whether oxidation is inhibited through controlling the environment of the API. This can be done in many ways, typically, for example, by means of capsules, tablet coatings and/or special packaging. It would be of great interest to know before evaluating the above commonly used means for preventing oxidation, however, whether the rate of oxidation actually could be inhibited or drastically slowed in the API by limiting its exposure to oxygen. This is done quite easily with the aforementioned devices 100, 101 and carousel 5 by additionally evaluating the API in an inert atmosphere at various temperatures.

The instant invention may be employed to augment another API or RS test protocol.

APIs or pharmaceutical compositions with API(s) may be for administration to humans and/or animals. An RS which may be generally inert such as with an excipient, for example, gum arabic or a starch; an ointment or cream base; or a tablet coating, for example, a wax or synthetic polymer; or which may be more active such as a transdermal carrier, for example, dimethyl sulfoxide—may be for application for humans and/or animals, and may otherwise be for application to plant life in which case the RS may be a growth stimulant or inhibitor, an herbicide, a fertilizer, and so forth and the like. Accordingly, an RS may be for accompanying an API or be employed independently of an API.

INCORPORATIONS BY REFERENCE

The specification, to include drawings, of the aforementioned provisional patent application No. 62/601,955 is incorporated herein by reference in its entirety. And, the specifications to include drawings, of the aforementioned U.S. Pat. Nos. 7,678,328 B1, 8,679,405 B1 and 8,975,083 B2, and U.S. patent application Ser. No. 14/121,952 and U.S. 62/390,774, are incorporated herein by reference in their entireties. U.S. Pat. No. 10,422,783 B2 has issued from U.S. application Ser. No. 16/350,253 as a divisional of U.S. application Ser. No. 14/121,952, and U.S. Pat. No. 10,302,619 B2 has issued from U.S. application Ser. No. 15/731,024, which claimed priority of application No. U.S. 62/390,774.

EPILOGUE

Accordingly, the invention can be embodied as the following embodiments:

A. A method of testing a sample of at least one API and/or at least one RS for stability comprising placing said sample in an instrument containing a pressure-controllable atmosphere, controlling the pressure of the atmosphere in the instrument for predetermined time, and evaluating the at least one API and/or the at least one RS of said sample for stability, wherein the testing is carried out:

under at least one predetermined temperature; and under the influence of at least one gaseous trigger, which is introduced to contact the sample under constant and/or ramped temperature(s) and elevated pressure(s) for one or more predetermined times, wherein the instrument is a bomb test instrument/reactor that is a rotatable bomb device, which has a housing with a hollow interior; a rotatable component located in the hollow interior, which is or includes an inner container that is rotated during at least part of the testing; and support for the rotatable component in the hollow interior.

B. The method of embodiment A, wherein the rotatable component is rotated during at least part of the testing by magnetic interaction of a magnet coupled to the rotatable component of the inner container and a rotating magnet driver outside the hollow interior.

C. The method of embodiment A, wherein said sample is or includes the at least one API; and the gaseous trigger is or includes gaseous oxygen.

D. The method of embodiment B, wherein said sample is or includes the at least one API; and the gaseous trigger is or includes gaseous oxygen.

E. The method of embodiment A, wherein the housing is stationary during the testing and has a substantially cylindrical wall defining a side boundary of the hollow interior in which the rotatable component is received; and the housing provides for a sealed bomb reactor with the rotatable inner container inside.

F. The method of embodiment B, wherein the housing is stationary during the testing; and the rotatable bomb device further includes at least one of:

an insulating lower disc or washer located at an inside bottom of the housing;

a plurality of staggered heating bands encompassing the housing, each of which is configured to be controlled or turned off independently;

a dry scan port in the housing, accessible from outside a front portion of the housing, into which a thermocouple or temperature sensor can be inserted and slid to any appropriate depth or position to tune or calibrate temperature;

a rear upper port and a rear lower port in the housing, each accessible from outside a rear portion of the housing, into each of which a thermocouple or temperature sensor can be inserted and slid to any appropriate depth or position; and an extraction/injection fitting for accessing the hollow interior of the housing through a lid thereto, said extraction/injection fitting including a tubular support system and a combination three-way valve and locking syringe system for employment therewith.

G, H, I, J, K and L. The method of embodiment A, B, C, D, E or F, respectively, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

CONCLUSION TO THE INVENTION

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous and sundry adaptations can be effected within its spirit, the literal claim scope of which is particularly pointed out by the following claims:

What is claimed is:

1. A method of testing a sample of at least one API and/or at least one RS for stability comprising placing said sample in an instrument containing a pressure-controllable atmosphere, controlling the pressure of the atmosphere in the instrument for a predetermined time, and evaluating the at least one API and/or the at least one RS of said sample for stability, wherein the testing is carried out:

under at least one predetermined temperature; and
under the influence of at least one gaseous trigger, which is introduced to contact
the sample under constant and/or ramped temperature(s) and elevated
pressure(s) for one or more predetermined times, wherein the instrument is a bomb test instrument/reactor that is a rotatable bomb device, which has a housing with a hollow interior; a rotatable component located in the hollow interior, which is or includes an inner container that is rotated during at least part of the testing; and support for the rotatable component in the hollow interior.

2. The method of claim 1, wherein the rotatable component is rotated by magnetic interaction of a magnet coupled to the rotatable component of the inner container and a rotating magnet driver outside the hollow interior.

3. The method of claim 1, wherein said sample is or includes the at least one API; and the gaseous trigger is or includes gaseous oxygen.

4. The method of claim 2, wherein said sample is or includes the at least one API; and the gaseous trigger is or includes gaseous oxygen.

5. The method of claim 1, wherein the housing is stationary during the testing and has a substantially cylindrical wall defining a side boundary of the hollow interior in which the rotatable component is received; and the housing provides for a sealed bomb reactor with the rotatable inner container inside.

6. The method of claim 2, wherein the housing is stationary during the testing; and the rotatable bomb device further includes at least one of:

an insulating lower disc or washer located at an inside bottom of the housing;
a plurality of staggered heating bands encompassing the housing, each of which is configured to be controlled or turned off independently;
a dry scan port in the housing, accessible from outside a front portion of the housing, into which a thermocouple or temperature sensor can be inserted and slid to any appropriate depth or position to tune or calibrate temperature;
a rear upper port in the housing, accessible from outside a rear portion of the housing, into which a thermocouple or temperature sensor can be inserted and slid to any appropriate depth or position;
a rear lower port in the housing, accessible from outside a rear portion of the housing, into which a thermocouple or temperature sensor can be inserted and slid to any appropriate depth or position; and
an extraction/injection fitting for accessing the hollow interior of the housing through a lid thereto, said extraction/injection fitting including a tubular support system and a combination three-way valve and locking syringe system for employment therewith.

7. The method of claim 1, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

8. The method of claim 2, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

9. The method of claim 3, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

10. The method of claim 4, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

11. The method of claim 5, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

12. The method of claim 6, wherein the rotatable component includes an insert carousel, which is employed for holding at least one of said sample and at least one aliquot of said sample for insertion into the rotatable bomb device, and the insert carousel is inserted into the hollow interior of the housing with the hollow interior oriented vertically along a central axis thereof.

* * * * *